(12) United States Patent
Kuhrs et al.

(10) Patent No.: US 8,415,265 B2
(45) Date of Patent: Apr. 9, 2013

(54) METHOD FOR PRODUCING MELAMINE

(75) Inventors: Christian Kuhrs, Heidelberg (DE); Andreas Kern, Mannheim (DE); Tilo John, Speyer (DE); Wolfgang Steiner, Friedelsheim (DE); Heiko Maas, Lantau Island (CN)

(73) Assignee: BASF SE (DE)

( * ) Notice: Subject to any disclaimer, the term of this patent is extended or adjusted under 35 U.S.C. 154(b) by 0 days.

(21) Appl. No.: 12/664,426

(22) PCT Filed: May 21, 2008

(86) PCT No.: PCT/EP2008/056223
§ 371 (c)(1),
(2), (4) Date: Dec. 14, 2009

(87) PCT Pub. No.: WO2008/151907
PCT Pub. Date: Dec. 18, 2008

(65) Prior Publication Data
US 2010/0184976 A1 Jul. 22, 2010

(30) Foreign Application Priority Data
Jun. 14, 2007 (EP) .................................. 07110305

(51) Int. Cl.
*B01J 29/06* (2006.01)
*C07D 251/12* (2006.01)
*C07D 251/60* (2006.01)
*C07D 251/62* (2006.01)

(52) U.S. Cl.
USPC .............. 502/66; 544/201; 544/203; 544/222

(58) Field of Classification Search .................... 502/66; 544/201, 203, 222
See application file for complete search history.

(56) References Cited

U.S. PATENT DOCUMENTS
7,253,280 B2    8/2007  Kuhrs et al.

FOREIGN PATENT DOCUMENTS
| WO | 92/09585 | * | 6/1992 |
| WO | WO-92/09585 A1 | | 6/1992 |
| WO | WO-2004/065371 A1 | | 8/2004 |

OTHER PUBLICATIONS

Yi Jiang et al., "Study on the Preparation of the Catalysts for Synthesis of Melamine From Urea", Natural Gas Chemical Industry, vol. 26, No. 2, pp. 23-25, 56, 2001.

* cited by examiner

*Primary Examiner* — James O Wilson
*Assistant Examiner* — Ebenezer O Sackey
(74) *Attorney, Agent, or Firm* — Connolly Bove Lodge & Hutz LLP

(57) ABSTRACT

A process for the preparation of melamine by decomposition of urea with the use of a catalyst, the catalyst comprising
a) 10-90% by weight of zeolite,
b) 10-90% by weight of a matrix comprising silica, alumina, silicon aluminum oxides and/or clay minerals, and
c) 0-10% by weight of additives
and the total content of nickel and vanadium in the catalyst being less than 500 ppm.

20 Claims, No Drawings

METHOD FOR PRODUCING MELAMINE

CROSS-REFERENCE TO RELATED APPLICATIONS

This application is a national stage application (under 35 U.S.C. §371) of PCT/EP2008/056223, filed May 21, 2008, which claims benefit of European application 07110305.5, filed Jun. 14, 2007.

BACKGROUND OF THE INVENTION

The invention relates to a process for the preparation of melamine by thermal decomposition of urea and catalytic conversion of the resulting isocyanic acid and the use of a special catalyst in such a process.

Melamine (2,4,6-triamino-1,3,5-triazine (I))

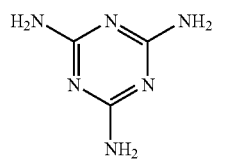

is used for the preparation of melamine resins by reaction with carbonyl-containing compounds. The resins are used, inter alia, as plastics and in paints and finishes. The preparation of melamine by decomposition of urea is a known reaction which is used in a plurality of variants by the chemical industry. In principle, a distinction is made between the high-pressure and the low-pressure process. The high-pressure process is carried out at pressures of >about 80 bar (abs.) and temperatures of >370° C., the melamine synthesis taking place in an uncatalyzed manner.

The low-pressure process is carried out at pressures of from about 1 to 10 bar (abs.) and temperatures of from 370 to 430° C. under catalysis. The reaction takes place in two steps. In the first, endothermic step, urea decomposes into ammonia and isocyanic acid, which is trimerized to melamine in the second, exothermic step with liberation of $CO_2$. The following equations reproduce the individual reactions.

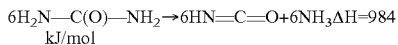

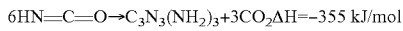

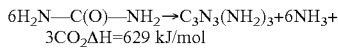

There are substantially three variants of the low-pressure process, which will be discussed in more detail below.

In the process of Linz Chemie, the reaction is carried out in two stages. In the first stage, molten urea at 350° C. and 3.5 bar (abs.) is decomposed in a fluidized sand bed to give ammonia and isocyanic acid. Isocyanic acid is then converted catalytically at 450° C. and atmospheric pressure in a fixed-bed reactor to give melamine. The catalyst is generally an alumina catalyst.

The DSM Stamicarbon process is a one-stage process which is carried out at about 7 bar (abs.). Catalysts used are aluminum silicates or zeolite-containing catalysts, which are used in a fluidized bed. Pure ammonia, which is recovered from the working-up stage, serves as fluidizing gas.

Finally, in the BASF process, the procedure is effected at low pressure (about 2 bar abs.), likewise in a fluidized bed, alumina or alumina/silica catalysts being used. Recycled gas originating from the reactor and comprising $NH_3$ and $CO_2$, which was freed from impurities beforehand, serves as gas for the fluidized bed.

Although the existing processes are used industrially, there is considerable room for improvements, for example with regard to the conversion in said low-pressure processes. Particularly with the use of a mixture of ammonia and carbon dioxide as a fluidizing gas, the conversions achieved are unsatisfactory in some cases.

It is therefore desirable to provide further catalysts for the melamine synthesis, by means of which the conversion of the process can be increased, particularly with the use of ammonia and $CO_2$ as fluidizing gas.

Thianranqi Huagong, 2001, Volume 26, pages 23 to 25 (cited according to CA 136:135396) discloses that active catalysts for melamine synthesis can be obtained by mixing $Al_2O_3$ with zeolites or zeolites with metal cations.

Zeolite-containing catalysts for the melamine synthesis are also obtainable from Albemarle Corporation (USA) under the name CAMEL 25®.

BRIEF SUMMARY OF THE INVENTION

The object of the invention is to provide a process by means of which high conversions and melamine yields are achievable, in particular with the use of a mixture of ammonia and $CO_2$.

The object is achieved by a process for the catalytic preparation of melamine by decomposition of urea over zeolite-containing catalysts which have a low content of nickel and vanadium.

The invention therefore relates to a process for the preparation of melamine by decomposition of urea with the use of a catalyst, the catalyst comprising a) 10-90% by weight of zeolite,
b) 10-90% by weight of a matrix comprising silica, alumina, silicon aluminum oxides and/or clay minerals, and
c) 0-10% by weight of additives and the total content of nickel and vanadium in the catalyst being less than 500 ppm.

The invention furthermore relates to the use of said catalyst for the preparation of melamine.

DETAILED DESCRIPTION OF THE INVENTION

With the process according to the invention, it is possible to achieve higher conversions in the melamine synthesis with constant high product quality.

The catalyst used according to the invention comprises, as main components, zeolite, a matrix of silica and/or alumina and/or clay minerals and, if appropriate, additives.

The zeolite component (a) preferably comprises synthetic zeolites of the faujasite type, particularly preferably Y-zeolites and silicon-rich Y-zeolites, if appropriate also as a mixture.

In general, zeolites which were subjected to ion exchange are used, i.e. the original sodium atoms are replaced by hydrogen and/or rare earth metals (RE) (H—, RE- or H, RE-Y zeolites). The proportion of sodium (as $Na_2O$) is in general <1% by weight. For the ion exchange, in general ammonium sulfate or rare earth metal chloride solutions are used for the H and RE form. The $NH_4$ form generally obtainable via ion exchange with ammonium sulfate solutions is heated for conversion into the H form, $NH_3$ escaping.

The proportion of the rare earth metals (as oxide $RE_2O_3$) is in general 0-20, preferably 0-15, % by weight. Preferred rare earth metals are lanthanum (La), cerium (Ce), neodymium (Nd) and praseodymium (Pr). A mixture of lanthanum and cerium with smaller proportions of neodymium and praseodymium is particularly preferred.

The Si/Al ratio of the zeolite is in general from 2 to 8, preferably from 3 to 6, in particular about 5, in the case of customary Y-zeolite and from 10 to 15, preferably from 11 to 12, in the case of silicon-rich Y-zeolites (SR-Y).

The size of the unit cell in the case of the Y-zeolites is in general from 2.460 nm to 2.465 nm and in the case of silicon-rich Y-zeolites about 2.450 nm. The size of the zeolite crystals is in general from 0.5 to 5 µm.

The zeolite component of the catalyst may also comprise mixtures of different zeolites, for example a mixture of Y-zeolite and silicon-rich Y-zeolite or additions of ZSM-5 zeolite, mordenite, off retite or silicalite.

The proportion of zeolite in the catalyst is in general from 10 to 90% by weight, preferably from 10 to 60% by weight, particularly preferably from 12.5 to 50% by weight, very particularly preferably from 15 to 40% by weight.

The zeolite component is prepared by known methods familiar to the person skilled in the art, as described, for example, in Atlas of Zeolite Structure Types, W. H. Meier and D. H. Olson, $3^{rd}$ edition, Butterworth-Heineman, 1992.

The zeolite component can, however, also be formed in situ together with the matrix component.

The matrix component (b) comprises silica, alumina, aluminosilicates and/or clay minerals. It is a porous, inorganic oxide matrix which binds the other components, ensures abrasion resistance and in certain circumstances itself contributes to the catalytic activity.

The matrix component (b) usually comprises a synthetic fraction, such as amorphous silica, alumina or aluminosilicate, and a natural fraction, usually one or more clay minerals. If the zeolite component is prepared in situ from calcined clay, the matrix component also usually comprises calcined clay.

The matrix comprises, if appropriate, boehmite, pseudoboehmite, diaspore, $\alpha$-, $\beta$-, $\gamma$-, $\delta$-, $\epsilon$-, $\eta$- and $\rho$-alumina or aluminum hydroxides, such as Gibbsite, Bayerite, Nordstrandite and Doyelite.

As further, natural constituents, the matrix component comprises, if appropriate, one or more, optionally modified clay minerals, such as kaolin, bentonite, attapulgite, montmorillonite, hectorite and pyrophyllite.

Before use in the matrix, the clay minerals are, if appropriate, subjected to a mild base or acid treatment in order to remove impurities and interfering metal ions. Calcination of the clay minerals, for example conversion of kaolin into a spinel/mullite mixture by calcination at about 1000° C. and subsequent leaching with base, is also customary.

The catalysts according to the invention generally have a BET surface area of 50-800, preferably 100-600, particularly preferably 150-400, $m^2/g$.

Four basic types of matrix component are preferred:
matrix components comprising amorphous silica,
matrix components which comprise amorphous alumina,
matrix components comprising amorphous aluminosilicates, all three stated types usually additionally comprising one or more natural clay minerals, and
matrix components comprising modified, preferably calcined clay minerals.

The proportion of the matrix, based on the catalyst used according to the invention, is in general from 10 to 90, preferably from 40 to 90, particularly preferably from 50 to 85, % by weight.

In addition to zeolite component and matrix component, the catalyst used according to the invention typically comprises from 0 to 10% by weight of additives.

For example, inorganic oxides, such as magnesium oxide, mixed oxides of rare earth metals and spinets, for example cerium-doped spinets, are suitable as such additives.

The catalysts used according to the invention are distinguished by a low content of Ni and V. The total content of these metals is <500 ppm, preferably <200 ppm, particularly preferably 100 ppm, very particularly preferably from 0 to 50 ppm. In particular, the catalyst is substantially free of Ni and V.

The catalyst is prepared by known processes familiar to the person skilled in the art. For example, the catalyst can be produced in a known manner from an inorganic sol with which the zeolite component and further additives have been mixed, by drying, ion exchange, calcination and subsequent steam treatment.

Matrix component and zeolite component of the catalyst generally have a different average pore size.

The average pore size of the matrix is in general 0.4-500 nm, preferably 0.5-250 nm, particularly preferably 5-50 nm.

The median particle size $d_{50}$ of the catalyst is in general less than 300 µm, preferably from 10 to 200 µm, particularly preferably from 40 to 100 µm, the fine fraction (d<10 µm) preferably being as small as possible.

For assessing the mechanical stability of the catalysts prepared with respect to the loads to which they would be exposed in a gas/solid fluidized bed, catalysts can be subjected to the abrasion test described below. It gives as a result an abrasion rate which describes the strength of the particles.

For determining the abrasion, about 20 g of an accurately weighed sample of the catalyst ($m_{0,\ catalyst}$), which is presieved using a 45 µm sieve, are introduced onto a 32 µm sieve having a diameter of 192 mm. A slotted nozzle (0.5 mm slot width) from which 100 $m^{3 \cdot -1}$ of nitrogen emerges at the speed of sound rotates at 32 rpm below the sieve at a distance of 10 mm. The catalyst accelerated by the nozzle jet strikes a Plexiglas cover which is present 8 mm above the sieve. The sample material is subjected to intensive mechanical stress thereby. The time of the experiment is 3 hours. The resulting abraded material (particles having diameters of <32 µm) emerges with the gas through the sieve fabric. The mass of the remaining particles is determined quantitatively at intervals of about 15 min by weighing. The abrasion rate AR, stated in $g \cdot kg^{-1} \cdot h^{-1}$, is obtained as the quotient of the mass loss within the last hour of the test $m_{abrasion}$ [$gh^{-1}$] and the mass of the catalyst still remaining after the end of the experiment $m_{catalyst\ after\ end\ of\ experiment}$ [kg]:

$$AR = (m_{abrasion}/m_{catalyst\ after\ end\ of\ experiment}).$$

The lower the abrasion rate, the higher is the mechanical stability of the catalyst. Catalysts suitable for fluidized-bed processes have an abrasion rate of less than 60 $g \cdot kg^{-1} \cdot h^{-1}$, preferably less than 30 $g \cdot kg^{-1} \cdot h^{-1}$.

The abrasion rate of the catalyst is in general <20 g/kgh, preferably <15 g/kgh, particularly preferably <10 g/kgh, in particular 1-7 g/kgh.

In general, the catalyst belongs to the so-called Geldard group A (D. Kunii, A. Levenspiel, Fluidization Engineering, $2^{nd}$ edition, Butterworth-Heinemann, 1991).

In the process according to the invention, in a first step, urea is decomposed thermally into isocyanic acid and ammonia and the isocyanic acid formed is then catalytically trimerized with liberation of $CO_2$ to give melamine.

Preferably, both reaction steps are carried out in one reactor, but they may also be effected in two separate reactors.

The process is preferably carried out as a fluidized-bed process. It is operated in general at temperatures of from 350 to 450° C., preferably from 380 to 420° C., an absolute pressure of in general from 1 to 15 bar, preferably from 1 to 10 bar, in particular from 1.5 to 8 bar, a residence time over the fluidized bed of from 1 to 50 s, preferably from 2 to 30 s, and a catalyst space velocity of from 20 to 700 kg of urea/t (cat.)·h, preferably from 50 to 500 kg of urea/t (cat.)·h.

The fluidizing gas used is pure $NH_3$ or an $NH_3/CO_2$ mixture, in the latter case the mixture forming during the synthesis being predominantly used.

The starting material urea is preferably introduced as a melt into the reactor.

In order to supply the energy required for the endothermic first reaction step, heat is supplied to the reaction mixture, preferably via heating coils in which a salt melt circulates.

An embodiment of the process according to the invention in which urea is converted into melamine in a fluidized-bed process with a mixture of $NH_3$ and $CO_2$ as fluidizing gas at a temperature of from 380 to 420° C. and an absolute pressure of from 1.5 to 8 bar in the presence of a catalyst according to the invention is preferred.

Catalyst particles can be retained in the reactor by cyclone separators.

The gaseous melamine formed in the synthesis is isolated from the fluidizing gas by quenching with aqueous mother liquor ("washing out with water") and subsequent crystallization or by cooling of the reaction gases with cold reaction gas (desublimation).

For example, the gas mixture from the reactor can be cooled in a first gas cooler to a temperature at which byproducts (e.g. melem) crystallize out and the precipitated byproducts are separated off in gas filters together with the catalyst dust present in the gas stream. The filtered gas stream can then be mixed in a crystallizer with process gas which has a temperature of about 140° C., the melamine crystallizing out in a purity of at least 99.9%.

The melamine thus prepared can in general be reacted directly without further purification steps, for example for the preparation of melamine resins by reaction with carbonyl compounds.

The invention is explained in more detail by the examples without it being intended to be limited thereby.

EXAMPLES

Urea was converted into melamine in a pilot reactor having a diameter of 50 cm and a catalyst bed height of about 3 m at a temperature of about 400° C. The amount of fluidizing gas ($NH_3/CO_2$) was about 110 m³(S.T.P.)/h. Fluidizing gas/urea ratio (FUR): 1.8; catalyst space velocity: 0.15 $g_{urea}/g_{catalyst}$·h. Pressure: 3 bar.

Three different catalyst types were used:

Catalyst 1 (comparative example 1) is a zeolite-containing catalyst commercially available for the melamine synthesis and having an MN content of 3900 ppm in the tested batch.

Catalyst 2 (comparative example 2) is a zeolite-free catalyst based on $SiO_2/Al_2O_3$ with an Ni/V content below the limit of detection, which was 100 ppm (method of measurement: X-ray fluorescence).

Catalyst 3 (example 1) is a zeolite-containing catalyst according to the invention which has an Ni/V content of <100 ppm.

The results are shown in Table 1. The conversion was determined via the melamine content and the amount of urea and standardized.

TABLE 1

|  | Comparative example 1 | Comparative example 2 | Example 1 |
|---|---|---|---|
| Standardized conversion [%] | 96 | 100 | 100 |
| Particle size (Geldart group) | A | B | A |
| Abrasion index [g/kg h] | 5 | 20 | 6 |

It is found that higher conversions can be achieved with the catalysts according to the invention than with the commercially available melamine catalyst. Although the zeolite-free catalyst has a conversion similar to that of the catalysts according to the invention, it has other disadvantages, such as particle size ("Geldart B" leads to poorer heat transfer coefficients and hence poorer heat transfer in the fluidized bed) and unfavorable abrasion index.

We claim:

1. A process for the preparation of melamine which comprises decomposing urea with a catalyst, wherein the catalyst comprises
   a) 10-90% by weight of zeolite,
   b) 10-90% by weight of a matrix comprising silica, alumina, silicon aluminum oxides and/or clay minerals, and
   c) 0-10% by weight of additives,
   the total content of nickel and vanadium in the catalyst being less than 500 ppm and the median particle size $d_{50}$ of the catalyst being less than 300 μm.

2. The process according to claim 1, the total content of nickel and vanadium in the catalyst being <200 ppm.

3. The process according to claim 1, the catalyst comprising a synthetic zeolite of the faujasite type.

4. The process according to claim 1, the proportion of the zeolite component in the catalyst being from 10 to 60% by weight.

5. The process according to claim 1, the catalyst having a BET surface area of from 50 to 800 m²/g.

6. The process according to claim 1, wherein the catalyst has an abrasion rate being <20 g/kg·h.

7. The process according to claim 1, the procedure being effected at temperatures in the range from 350 to 650° C. and an absolute pressure of from 1 to 15 bar.

8. The process according to claim 1, the procedure being effected in a fluidized bed.

9. The process according to claim 8, the procedure being effected with a mixture of $NH_3$ and $CO_2$ as fluidizing gas.

10. The process according to claim 1, wherein the catalyst consists essentially of
    a) 10-90% by weight of zeolite,
    b) 10-90% by weight of a matrix comprising silica, alumina, silicon aluminum oxides and/or clay minerals, and
    c) 0-10% by weight of additives,
    the total content of nickel and vanadium in the catalyst being less than 500 ppm and the median particle size $d_{50}$ of the catalyst being less than 300 μm.

11. The process according to claim 1, wherein the catalyst consists of
    a) 10-90% by weight of zeolite,
    b) 10-90% by weight of a matrix comprising silica, alumina, silicon aluminum oxides and/or clay minerals, and
    c) 0-10% by weight of additives, the total content of nickel and vanadium in the catalyst being less than 500 ppm and the median particle size $d_{50}$ of the catalyst being less than 300 μm.

12. A catalyst which consists essentially of
a) 15-40% by weight of zeolite,
b) 50-85% by weight of a matrix comprising silica, alumina, silicon aluminum oxides and/or clay minerals, and
c) 0-10% by weight of additives which are selected from the group consisting of an inorganic oxide and a mixed oxide of rare earth metals and spinels,
the total content of nickel and vanadium in the catalyst being from 0 to 50 ppm and the median particle size $d_{50}$ of the catalyst being from 40 to 100 μm and the average pore size of the matrix is from 5 to 50 nm.

13. A catalyst for the preparation of melamine comprising
a) 10-90% by weight of zeolite,
b) 10-90% by weight of a matrix comprising silica, alumina, silicon aluminum oxides and/or clay minerals, and
c) 0-10% by weight of additives, and
wherein the total content of nickel and vanadium in the catalyst being less than 500 ppm and the median particle size $d_{50}$ of the catalyst being less than 300 μm.

14. The catalyst according to claim 13, the total content of nickel and vanadium in the catalyst being <200 ppm.

15. The catalyst according to claim 13, the catalyst comprising a synthetic zeolite of the faujasite type.

16. The catalyst according to claim 13, the proportion of the zeolite component in the catalyst being from 10 to 60% by weight.

17. The catalyst according to claim 13, the catalyst having a BET surface area of from 50 to 800 $m^2/g$.

18. The catalyst according to claim 13, wherein the catalyst has an abrasion rate being <20 g/kg·h.

19. The catalyst according to claim 13 which consists essentially of
a) 10-90% by weight of zeolite,
b) 10-90% by weight of a matrix comprising silica, alumina, silicon aluminum oxides and/or clay minerals, and
c) 0-10% by weight of additives,
the total content of nickel and vanadium in the catalyst being less than 500 ppm and the median particle size $d_{50}$ of the catalyst being less than 300 μm.

20. The catalyst according to claim 13 which consists of
a) 10-90% by weight of zeolite,
b) 10-90% by weight of a matrix comprising silica, alumina, silicon aluminum oxides and/or clay minerals, and
c) 0-10% by weight of additives,
the total content of nickel and vanadium in the catalyst being less than 500 ppm and the median particle size $d_{50}$ of the catalyst being less than 300 μm.

* * * * *